United States Patent [19]

Dirlikov et al.

[11] Patent Number: 4,581,465
[45] Date of Patent: Apr. 8, 1986

[54] PREPARATION OF 1,4-LACTONES OF 3,6-ANHYDROHEXANOIC ACIDS

[75] Inventors: Stoil K. Dirlikov; Connie J. Schneider, both of Midland, Mich.

[73] Assignee: The Dow Chemical Company, Midland, Mich.

[21] Appl. No.: 590,130

[22] Filed: Mar. 16, 1984

[51] Int. Cl.$^4$ ............................................. C07D 305/12
[52] U.S. Cl. .................................................... 549/306
[58] Field of Search ........................................ 549/306

[56] References Cited

U.S. PATENT DOCUMENTS 1,985,255  12/1934  Isbell ................................. 562/580

OTHER PUBLICATIONS

*Glucurolactone,* Chemical Division, Corn Products Refining Co., p. 2, Publication Circa, 1952.
*Merck Index* (10th Edition, 1983) Gluconic Acid, Substance No. 4316, p. 638.
Merck Index (10th Edition, 1983) D-Glucuronolactone, Substance No. 4329, pp. 640-641.
Haworth et al., J. Chem. Soc. (London), 88 (1941).

*Primary Examiner*—Paul R. Michl
*Assistant Examiner*—Alex H. Walker

[57] ABSTRACT

The invention is a process for the preparation of a 1,4-lactone of 3,6-anhydrohexanoic acid which comprises refluxing a 1,4- or 1,5-lactone of pentahydroxyhexanoic acid, or an aqueous solution of pentahydroxyhexanoic acid in an organic reaction media which azeotropes with water in the presence of an inorganic acid, under conditions such that a 1,4-lactone of 3,6-anhydrohexanoic acid is formed.

14 Claims, No Drawings

PREPARATION OF 1,4-LACTONES OF 3,6-ANHYDROHEXANOIC ACIDS

BACKGROUND OF THE INVENTION

The invention relates to a process for the preparation of 1,4-lactones of 3,6-anhydrohexanoic acids from pentahydroxyhexanoic acids.

The 1,4-lactones of 3,6-anhydrohexanoic acids are useful as polyols in the preparation of polyurethanes. See Dirlikov et al., U.S. Pat. No. 4,438,226.

Haworth et al., *J. Chem. Soc. I*, 88 (1941), disclose a process for the preparation of 1,4-lactones of 3,6-anhydrohexanoic acids. The reference discloses heating a solution of monoacetone 3,6-anhydroglucofuranose in 1N sulfuric acid for 1 hour and then neutralizing the solution with barium carbonate, filtering and evaporating to dryness under reduced pressure to give a syrup which quickly crystallizes. Upon purification, the product is 3,6-anhydroglucose. The anhydroglucose is thereafter oxidized in water with bromine at room temperature for 6 days to afford 3,6-anhydro-1,4-gluconolactone.

Ohle et al., *Chem. Ber.*, 61, 1203 (1928), disclose the preparation of the monoacetone of 3,6-anhydroglucofuranose from glucose in a multistep synthesis.

The preparation of 1,4-lactones of 3,6-anhydrohexanoic acids requires a complicated multistep synthesis. What is needed is a simple and direct process for the preparation of 1,4-lactones of 3,6-anhydrohexanoic acids.

SUMMARY OF THE INVENTION

The invention is a process for the preparation of a 1,4-lactone of 3,6-anhydrohexanoic acid which comprises refluxing a 1,4- or 1,5-lactone of pentahydroxyhexanoic acid, or an aqueous solution of a pentahydroxyhexanoic acid, in an organic reaction medium, which azeotropes with water, in the presence of an inorganic acid, under conditions such that a 1,4-lactone of 3,6-anhydrohexanoic acid is formed.

The process of this invention surprisingly allows the direct synthesis of 1,4-lactones of 3,6-anhydrohexanoic acids from pentahydroxyhexanoic acid and 1,4- and 1,5-lactones of pentahydroxyhexanoic acids.

DETAILED DESCRIPTION OF THE INVENTION

The starting materials of this invention are 2,3,4,5,6-pentahydroxyhexanoic acids. There are 16 isomers of 2,3,4,5,6-pentahydroxyhexanoic acids of which only those in which one of the hydroxy groups on the 3 and 4 carbons is d while the other hydroxy group is 1, are useful in preparing the 1,4-lactone of 3,6-anhydrohexanoic acids. The preferred isomer is gluconic acid, which is the most common isomer. The 1,4- and 1,5-lactones of pentahydroxyhexanoic acids revert to pentahydroxyhexanoic acids when dissolved in aqueous solution. The pentahydroxyhexanoic acids are only present in the acidic form when dissolved in aqueous solution.

The 1,4-lactones of pentahydroxyhexanoic acids generally correspond to the formula

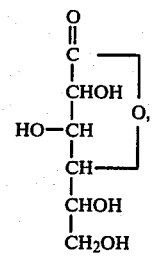

and the 1,5-lactones of pentahydroxyhexanoic acids correspond to the formula

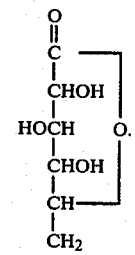

Pentahydroxyhexanoic acids generally correspond to the formula

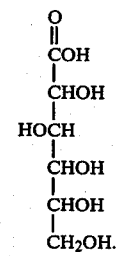

In one embodiment of this invention, the starting compound can be the pentahydroxyhexanoic acid. In this embodiment an aqueous solution of pentahydroxyhexanoic acid is contacted with an organic reaction medium in the presence of an inorganic acid catalyst and the reaction mixture is refluxed so as to prepare the 1,4-lactone of 3,6-anhydrohexanoic acid. During this process, both the 1,4-lactone ring and the 3,6-anhydro ring are formed. The formation of these rings results in a product which is soluble in the organic phase and will remain in that phase.

The product of this invention is a 1,4-lactone of 3,6-anhydrohexanoic acid. The preferred 1,4-lactone of 3,6-anhydrohexanoic acid is the 1,4-lactone of 3,6-anhydrogluconic acid. In the embodiment wherein the starting material is a 1,5-lactone of pentahydroxyhexanoic acid, the 1,5-lactone ring rearranges to form a 1,4-lactone ring before the 3,6-anhydro ring is formed. 1,4-Lactones of 3,6-anhydrogluconic acids generally correspond to the formula

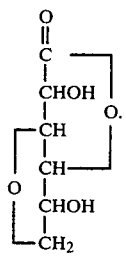

The difference between the 1,4-lactones derived from the different isomers is in the geometry of the particular 1,4-lactones. The 1,4-lactones of 3,6-anhydrogluconic acid are the most preferred 1,4-lactones because gluconic acid is the most readily available starting material.

In general, the process of this invention involves contacting a solution of the 1,4- or 1,5-lactone of pentahydroxyhexanoic acid in the organic reaction medium at reflux with an inorganic acid catalyst, or contacting an organic reaction medium with an aqueous solution of pentahydroxyhexanoic acid at reflux in the presence of an inorganic acid catalyst.

Catalysts useful in this reaction are inorganic acids. Preferred inorganic acids include hydrochloric acid, furic acid, sulfonic acids and sulfuric acids. More preferred inorganic acids are sulfuric or sulfonic acids, with sulfonic acids being most preferred. Examples of preferred sulfonic acids include p-toluene sulfonic acid and benzene sulfonic acid.

In one preferred embodiment, the inorganic acid is a pendant moiety on the backbone of a polymeric structure. In a more preferred embodiment, the catalyst is a copolymer of divinylbenzene and styrene with pendant sulfonate moieties. Examples of such catalysts include the DOWEX®50 and DOWEX®HGR-W resins (available from The Dow Chemical Company, Midland, Mich.

An amount of catalyst sufficient to catalyze the reaction is suitable for this process. Preferably between about 0.1 and 10 weight percent of the catalyst based upon the starting reactant is used to catalyze this reaction. More preferably, the amount of catalyst used is between 1 and 10 percent by weight of the catalyst based on the starting reactant. Wherein the catalyst is a pendant moiety on a polymeric backbone, weight percent refers to the weight of the acid moieties.

This process can be run at any temperature at which the reaction proceeds. Preferable temperatures are between 50° C. and 200° C., with between about 70° C. and 150° C. being most preferred. Above 200° C. the 1,4-lactones of 3,6-anhydrohexanoic acid undergo decomposition. Below 50° C. the reaction rate is extremely slow.

Organic reaction media useful in this process include organic solvents which azeotrope with water at reflux at a temperature at which this reaction will proceed. Preferred organic reaction media include the aromatic hydrocrbons, chlorinated aromatic hydrocarbons and chlorinated aliphatic hydrocarbons. Examples of aromatic hydrocarbons include benzene, toluene, xylene, ethylbenzene and the like. Examples of chlorinated aromatic hydrocarbons include monochlorobenzenes, dichlorobenzenes, trichlorobenzenes, monochlorotoluene, monochloroethylbenzene, and the like. Examples of chlorinated aliphatic hydrocarbons include chloromethane, dichloromethane, trichloromethane, tetrachloromethane, chloroethane, dichloroethane, 1,1,1-trichloroethane, vinyl chloride, vinylidene chloride and the like. The preferred organic reaction media are the aromatic hydrocarbons, with toluene being most preferred.

A sufficient amount of organic reaction media for this reaction is between about 0.1 and 2.0 liters/mole of starting reactant, preferably between 0.5 and 1.0 liter/mole of starting reactant.

The formation of the anhydro rings results in the preparation of water as a by-product. In the embodiment wherein no water is introduced into the reactor, the process is run at reflux of the reaction mixture in a manner such that the water and organic reaction media is azeotroped away from the reaction mixture. The water and organic reaction media can be separated upon condensation of the azeotrope and the organic reaction media returned to the reaction solution. In this embodiment, the reaction is run until the formation of water ceases as this indicates the reaction has reached completion. Removal of the water from the reaction zone results in driving the equilibrium reaction in the formation of the 3,6-anhydro ring to the left, or in the direction of the product.

In the embodiment wherein the starting reactant is a pentahydroxyhexanoic acid which is dissolved in aqueous solution, the process is run in a manner such that all of the water is removed through azeotropic distillation. In this embodiment, the product will remain in the organic phase left behind.

The reaction time for this process can be any reaction time which gives the desired yield of product. Preferable reaction times are between about 1 and 20 hours, with between about 2 and 10 hours being most preferred.

In order to recover the reaction product from the organic reaction media left behind, the catalyst must first be removed from the reaction mixture. Wherein the catalyst is a pendant moiety on a polymeric backbone, the catalyst can be removed by filtration. In the embodiment where the inorganic acid is not bound to a polymeric backbone, the acid may be neutralized using a sodium or potassium carbonate in an amount sufficient to neutralize the acid. Once the catalyst has been removed or neutralized, then the reaction solution can be distilled to separate the solvent from the product.

The pentahydroxyhexanoic acids can be produced by oxidation of pentahydroxyhexanals which can be refined from white sugars, cellulosic materials and the like. Gluconic acid, the preferred starting material, is industrially produced by the oxidation of glucose derived from waste sugars.

SPECIFIC EMBODIMENTS

The following example is included for illustrative purposes only and does not limit the scope of the invention or the scope of the claims. All parts and percentages are by weight unless otherwise stated.

EXAMPLE 1,5-Lactone of gluconic acid (50.0 g), DOWEX®50WX4 (5.0 g) (a styrene divinylbenzene copolymer with pendant sulfonate moieties) and toluene (500 ml) are loaded into a flask equipped with Dean-Stark adaptor for water separation. The mixture is refluxed for 5 hours and cooled. Toluene is separated by decantation and the residue dissolved in 500 ml of methanol. The solution is filtered several times for separation of the DOWEX® resin and methanol distilled on a rotavapor. The 1,5-lactone of anhydrogluconic acid is isolated by vacuum distillation using a Kugelrohr distillation apparatus at 160° C. to 170° C. at a pressure of 0.2 mm mercury. The 1,4-lactone of 3,6-anhydrogluconic acid is obtained in a 27 percent yield, 11.5 g. Large prisms with a melting point of 117° C. are obtained by recrystallization from ethyl acetate.

What is claimed is:

1. A process for the preparation of a 1,4-lactone of 3,6-anhydro-2,3,4,5,6-pentahydroxyhexanoic acid which comprises refluxing a 1,4- or 1,5-lactone of pentahydroxyhexanoic acid, or an aqueous solution of pentahydroxyhexanoic acid, in an organic reaction medium which azeotropes with water, in the presence of an inorganic acid, under conditions such that a 1,4-lactone of 3,6-anhydro-2,3,4,5,6-pentahydroxyhexanoic acid is formed.

2. The process wherein the 1,4- or 1,5-lactone of pentahydroxyhexanoic acid is a 1,4- or 1,5-lactone of gluconic acid, the pentahydroxyhexanoic acid is gluconic acid and the 1,4-lactone of 3,6-anhydro-2,3,4,5,6-pentahydroxyhexanoic acid is the 1,4-lactone of 3,6-anhydrogluconic acid.

3. The process of claim 2 wherein the 1,4-lactone of gluconic acid corresponds to the formula

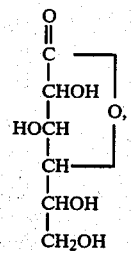

the 1,5-lactone of gluconic acid corresponds to the formula

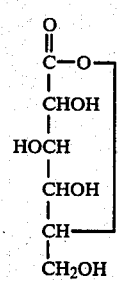

gluconic acid corresponds to the formula

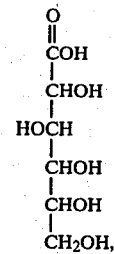

and the 1,4-lactone of 3,6-anhydrogluconic acid corresponds to the formula

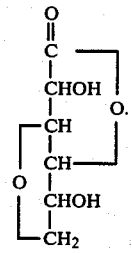

4. The process of claim 3 wherein the catalyst is hydrochloric acid, a furic acid, a sulfonic acid or a sulfuric acid.

5. The process of claim 4 wherein the catalyst is a sulfonic acid.

6. The process of claim 5 wherein the sulfonic acid is present as a pendant moiety on a polymeric backbone.

7. The process of claim 6 wherein the catalyst is a copolymer of styrene and divinylbenzene which contains pendant sulfonate moieties.

8. The process of claim 5 wherein the reflux temperature is between about 50° C. and 200° C.

9. The process of claim 8 wherein the organic reaction medium is a chlorinated aromatic hydrocarbon, a chlorinated aliphatic hydrocarbon or an aromatic hydrocarbon.

10. The process of claim 9 wherein the organic reaction medium is toluene.

11. A process for the preparation of the 1,4-lactone of 3,6-anhydrogluconic acid which comprises refluxing an aqueous solution of pentahydroxy hexanoic acid and toluene in the presence of sulfonic acid, which is present as a pendant moiety on the backbone of a copolymer of styrene and divinyl benzene.

12. The process of claim 11 wherein the amount of sulfonic acid used is between 1 and 10 percent by weight of starting material.

13. The process of claim 12 wherein the reaction time is between 2 and 10 hours.

14. The process of claim 13 wherein the reaction temperature is between 70° C. and 150° C.

* * * * *